(12) United States Patent
Souda et al.

(10) Patent No.: US 6,909,013 B2
(45) Date of Patent: Jun. 21, 2005

(54) PROCESS FOR PRODUCING CYCLOPROPANECARBOXYLATES

(75) Inventors: Hiroshi Souda, Takatsuki (JP); Kazunori Iwakura, Ibaraki (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 10/053,680

(22) Filed: Jan. 24, 2002

(65) Prior Publication Data

US 2002/0151741 A1 Oct. 17, 2002

(30) Foreign Application Priority Data

Jan. 24, 2001 (JP) .................................. 2001-016106
Jan. 24, 2001 (JP) .................................. 2001-016107

(51) Int. Cl.$^7$ ................................................ C07C 69/24
(52) U.S. Cl. ............................................................ 560/124
(58) Field of Search ........................................... 560/124

(56) References Cited

U.S. PATENT DOCUMENTS

| 4,547,522 A | 10/1985 | Martel et al. |
| 6,034,128 A | 3/2000 | Ujihara |

FOREIGN PATENT DOCUMENTS

| EP | 0 779 269 A1 | 6/1997 |
| HU | 220277 B | 5/2000 |
| JP | 11-228491 | 8/1999 |
| SA | 9610519 | 12/1996 |

OTHER PUBLICATIONS

Armin de Meijere et al., J. Org. Chem. vol. 58, pp. 502–505, 1993.
Ishihara et al., *Direct Condensation of Carboxylic Acids...*, Science, vol. 290, Nov. 10, 2000, pp. 1140–1142.
Dimmock, Paul et al., J. Chem. Soc., Chem. Commun., 1994, pp. 2323–2324.

*Primary Examiner*—Deborah C. Lambkin
*Assistant Examiner*—Andrea D. Small
(74) *Attorney, Agent, or Firm*—Birch, Stewart, Kolasch & Birch, LLP

(57) ABSTRACT

There is disclosed a process process for producing a cyclopropanecarboxylate of formula (1):

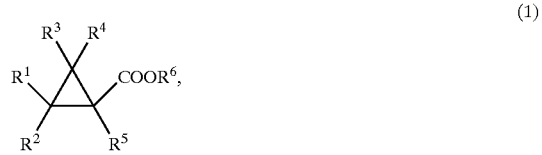

(1)

which process comprises reacting cyclopropanecarboxylic acid of formula (2):

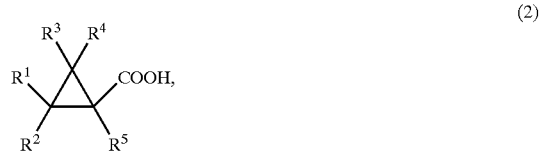

(2)

with a monohydroxy compound of formula (3):

$R^6OH$ (3), in the presence of a catalyst compound comprising an element of to Group 4 of the Periodic Table of Elements.

31 Claims, No Drawings

PROCESS FOR PRODUCING CYCLOPROPANECARBOXYLATES

FIELD OF THE INVENTION

The present invention relates to a process for producing cyclopropanecarboxylates.

BACKGROUND OF THE INVENTION

There have been known a production method of carboxylic acid ester from a carboxylic acid and an alcohol using a protonic acid catalyst. A production method using sulfuric acid as a catalyst is disclosed (Japanese Patent Laid-Open Publication No. 9-188649), and also disclosed is a method of using p-toluenesulfonic acid as a catalyst (Japanese Patent Laid-Open Publication No. 11-228491).

However, the methods using mineral acid or organic acid having strong acidity cause significant coloring due to a side reaction, which has made these methods not necessarily efficient as industrial production methods.

SUMMARY OF THE INVENTION

According to the present invention, a cyclopropanecarboxylate can be conveniently produced, through dehydration reaction, from a cyclopropanecarboxylic acid and an alcohol in the presence of the catalyst as defined below.

The present invention provides a process for producing a cyclopropanecarboxylate of formula (1):

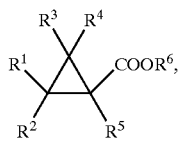
(1)

which process comprises reacting
a cyclopropanecarboxylic acid of formula (2):

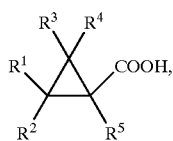
(2)

with a monohydroxy compound of formula (3):

 (3), in the presence of
a compound comprising an element of Group 4 of the Periodic Table of Elements,
wherein in formula (1) and (2),
$R^1$, $R^2$, $R^3$, $R^4$, and $R^5$ independently represent
a hydrogen atom, a halogen atom,
an alkyl group which may be substituted,
an alkenyl group which may be substituted,
an alkynyl group which may be substituted,
an aryl group which may be substituted; and
in formula (3),
$R^6$ represents
an alkyl group which may be substituted, or
an aryl group which may be substituted.

DETAILED DESCRIPTION OF THE INVENTION

The halogen atom or the term "halo" in the present specification means a fluorine atom, a chlorine atom, a bromine atom, or an iodine atom in $R^1$ through $R^6$.

The alkyl group which may be substituted and the alkenyl group which may be substituted may be linear, branched, or cyclic.

The term alkenyl or alkynyl in $R^1$ through $R^6$ and substituents that may be present therein means the same group as specified for $R^1$ to $R^5$ below.

The aryl group represented by $R^1$ through $R^6$ and the "aryl" including those present as the substituent group as in aryloxy, or haloaryloxy includes a (C6–C14)aryl group such as phenyl, biphenyl, naphthyl, anthracenyl or the like.

$R^1$, $R^2$, $R^3$, $R^4$, and $R^5$ in the cyclopropanecarboxylic acid (2) and the cyclopropanecarboxylate (1) will be explained below.

Examples of the alkyl group which may be substituted represented by $R^1$, $R^2$, $R^3$, $R^4$, or $R^5$ include, for example, a (C1–10) alkyl group such as methyl, ethyl, n-propyl, i-propyl, n-butyl, sec-butyl, tert-butyl, n-pentyl, n-hexyl, cyclohexyl, n-heptyl, n-octyl, n-nonyl, n-decyl, menthyl and the like.

Examples of the alkenyl group which may be substituted represented by $R^1$, $R^2$, $R^3$, $R^4$, or $R^5$ include, for example, a (C2–C5) alkenyl group such as vinyl, 1-methylvinyl, 1-propenyl, 2-methyl-1-propenyl, 1-butenyl, 3-methyl-2-butenyl or the like.

The alkyl group, alkenyl and alkynyl groups represented by $R^1$, $R^2$, $R^3$, $R^4$, or $R^5$ may be independently substituted with at least one member selected from halogen atom, an alkoxy group, an alkoxycarbonyl group, a haloalkoxycarbonyl group, an aryl group, a halocycloalkylidene group, an alkoxyimino group, an alkylsulfonyl group, an alkylsulfonyloxy group, and a hydroxysulfinyl group.

Examples of the alkenyl group substituted with halogen include, a halo (C2–C5) alkenyl group such as 2,2-dichlorovinyl, 2,2-dibromovinyl, 2-chloro-2-fluorovinyl, 2-chloro-2-trifluoromethylvinyl, 2 bromo-2-tribromomethylvinyl, or the like.

Examples of the alkynyl group which may be substituted includes a propargyl group and the like.

Examples of the alkoxy group include, for example, a (C1–C4) alkoxy group such as methoxy, ethoxy, n-propoxy, i-propoxy, n-butoxy, sec-butoxy, or tert-butoxy group or the like.

Examples of the alkoxycarbonyl group include, for example, a (C1–C4)alkoxy-carbonyl such as methoxycarbonyl, ethoxycarbonyl, n-propoxycarbonyl, i-propoxycarbonyl, n-butoxycarbonyl, sec-butoxycarbonyl, tert-butoxycarbonyl or the like.

Examples of the haloalkoxycarbonyl group include for example, a halo(C1–C4)alkoxy-carbonyl group such as a 2,2,2-trifluoro-1-(trifluoromethyl)ethoxycarbonyl group or the like.

Preferred aryl group are phenyl, 1-naphthyl, and 2-naphthyl groups and the like.

Examples of the halocycloalkylidene group include, for example, a halo (C3–C5)cycloalkylidene group such as difluorocyclopropylidene group or the like.

Examples of the alkoxyimino group include, for example, a (C1–C3) alkoxy-imino group such as methoxyimino, ethoxyimino, an n-propoxyimino or the like.

Examples of the alkylsulfonyl group include, for example, a (C1–C4) alkylsulfonyl group such as methylsulfonyl, ethylsulfonyl, n-propylsulfonyl, i-propylsulfonyl, tert-butylsulfonyl or the like.

Examples of the alkylsulfonyloxy group include, for example, a (C1–C4)alkylsulfonyloxy group such as methylsulfonyloxy, ethylsulfonyloxy, n-propylsulfonyloxy, i-propylsulfonyloxy, tert-butylsulfonyloxy or the like.

The cyclopropanecarboxyic acid (2) includes any optical isomer or mixture thereof.

Specific examples of the cyclopropanecarboxylic acid (2) include, for example, cyclopropanecarboxylic acid,
2-fluorocyclopropanecarboxylic acid,
2,2-dichlorocyclopropanecarboxylic acid,
2,2-dimethyl-3-(dimethoxymethyl cyclopropanecarboxylic acid,
2,2,3,3-tetramethylcyclopropanecarboxylic acid,
2,2-dimethyl-3-(1-propenyl)cyclopropanecarboxylic acid;
2,2-dimethyl-3-(2-methyl-1-propenyl)cyclopropanecarboxylic acid,
2,2-dimethyl-3-(3-methyl-2-butenyl)cyclopropanecarboxylic acid,
2,2-dimethyl-3-(2,2-dichlorovinyl)cyclopropanecarboxylic acid,
2,2-dimethyl-3-(2,2,2-trichloroethyl)cyclopropanecarboxylic acid,
2,2-dimethyl-3-(2-chloro-2-fluorovinyl)cyclopropanecarboxylic acid,
2,2-dimethyl-3-(2-bromovinyl)cyclopropanecarboxylic acid,
2,2-dimethyl-3-(2,2-dibromovinyl)cyclopropanecarboxylic acid,
2,2-dimethyl-3-(1,2,2,2-tetrabromoethyl)cyclopropanecarboxylic acid,
2,2-dimethyl-3-(1,2-dibromo-2,2-dichloroethyl)cyclopropanecarboxylic acid,
2,2-dimethyl-3-(2-chloro-3,3,3-trifluoro-1-propenyl)cyclopropanecarboxylic acid,
2,2-dimethyl-3-{3,3,3-trifluoro-2-(trifluoromethyl)-1-propenyl}cyclopropanecarboxylic acid,
2,2-dimethyl-3-(2-phenyl-1-propenyl)cyclopropanecarboxylic acid,
2,2-dimethyl-3-(2-phenylvinyl)cyclopropanecarboxylic acid,
2,2-dimethyl-3-(2-methyl-3-phenyl-2-butenyl)cyclopropanecarboxylic acid,
2,2-dimethyl-3-{(2,2-difluorocyclopropylidene)methyl}cyclopropanecarboxylic acid,
2,2-dimethyl-3-{2-(tert-butoxycarbonyl)vinyl}cyclopropanecarboxylic acid,
2,2-dimethyl-3-{2-fluoro-2-(methoxycarbonyl)vinyl}cyclopropanecarboxylic acid,
2,2-dimethyl-3-{2-fluro2-(ethoxycarbonyl)vinyl}cyclopropanecarboxylic acid,
2,2-dimethyl-3-{2-fluoro2-(tert-butoxycarbonyl)vinyl}cyclopropanecarboxylic acid,
2,2-dimethyl-3-[2-{2,2,2-trifluoro-1-(trifluoromethyl)ethoxycarbonyl}vinyl]cyclopropanecarboxylic acid,
2,2-dimethyl-3-(2-aza-2-methoxyvinyl)cyclopropanecarboxylic acid,
2,2-dimethyl-3-(4-aza-4-methoxy-3-methylbut-1,3-dienyl)cyclopropanecarboxylic acid,
2,2-dimethyl-3-[2-{(tert-butyl)sulfonyl}-2-(tert-butoxycarbonyl)vinyl]cyclopropanecarboxylic acid,
2,2-dimethyl-3-{2,2,2-tribromo-1-(methylsulfonyloxy)ethyl}cyclopropanecarboxylic acid,
2,2-dimethyl-3-{2,2-dibromo-2-(hydroxysulfinyl)-1-(methoxy)-ethyl}cyclopropanecarboxylic acid,
2,2-dimethyl-3-{2,2,2-tribromo-1-((methylsulfonyloxy)ethyl}-cyclopropanecarboxylic acid,
2-methyl-2-ethyl-3-(1-propenyl)cyclopropanecarboxylic acid,
2,2-diethyl-3-(2,2-dichlorovinyl)cyclopropanecarboxylic acid, and
2-methyl-2-phenyl-3-(2-methyl-1-propenyl) cyclopropanecarboxylic acid.

Preferred are 2,2-dimethyl-3-(2,2-dichlorovinyl) cyclopropanecarboxylic acid, and 2,2-dimethyl-3-(2-methyl-1-propenyl)cyclopropanecarboxylic acid.

Next a description will be made to the monohydroxy compound of formula (3).

Examples of the alkyl group, which may be substituted, represented by $R^6$, include, for example,
a (C1–C10) alkyl group which may be substituted with a member selected from
a halogen atom, a cyano group, a nitro group,
an alkenyl group, a haloalkenyl group, an alkynyl group, or
an aryl or heterocyclic group which may be substituted with at lest one member selected from
an alkyl group, a haloalkyl group,
an alkoxy group, a haloalkoxy group,
an alkoxyalkyl group,
an alkenyl group, an alkynyl group,
an aryl group, an aryoxy group,
a haloaryloxy group, an aralkyl group (e.g. (C7–C8) aralkyl such as benzyl, phenethyl),
an acyl group (e.g. (C1–C2)acyl such as formyl, acetyl),
a haloacyloxyalkyl group (e.g. trifluoroacetyloxyalkyl),
an amino group, and a halogen atom; or
$R^6$ represents:
a 1-, or 2-indanyl group which may be substituted with an alkynyl group or an aryl or heteroaryl group (e.g. 5- or 6-membered heteroaryl group such as thienyl); or
a cycloalkenyl group (e.g. cyclopentenyl) substituted with at least one member selected from an oxo group, an alkyl group, an alkenyl and an alkynyl group (e.g. 4-hydroxy-3-methyl-2-(2-propenyl)-2-cyclopentene-1-one, 4-hydroxy-3-methyl-2-(2-propynyl)-2-cyclopentene-1-one).

The term "alkyl" used in the alkyl, haloalkyl, and alkoxyalkyl groups as recited in the definition of $R^6$ and substituents thereof includes a C1–C14 alkyl group.

Examples of the (C1–C14) alkyl group include, for example,
methyl, ethyl, n-propyl, isopropyl, n-butyl, sec-butyl, tert-butyl, n-pentyl, neopentyl, n-hexyl, n-octyl, n-nonyl, n-decyl, undecyl, dodecyl, tridecyl, tetracecyl group and the like.

Examples of the haloalkyl group include fluoroethyl, difluoroethyl, trifluoroethyl, tetrafluoroethyl and the like.

The term "alkoxy" used in the alkoxy, haloalkoxy, and alkoxyalkyl groups includes a C1–C4 alkoxy group as defined above in this specification.

Examples of the alkenyl groups as recited above include a (C2–C5)alkenyl group (e.g. vinyl, 1-propenyl, 1-methyl-2-propenyl, 1-butenyl, 2-penten-2-yl group) or the like). The haloalkenyl group that may be present on the alkyl group represented by $R^6$ means the same haloalkenyl group as described for the haloalkenyl group represented by $R^1$ to $R^5$.

Examples of the alkynyl groups that may be present on the alkyl group represented by $R^6$ include a (C2–C5)alkynyl group (e.g, ethinyl, propynyl, butynyl, pentynyl or the like).

Examples of the heterocyclic group which may be substituted, include, for example, a furyl group, an isoxazolyl group, a pyrrolyl group, a thiazolyl group, an imidazolidine-2,4-dione group, a 4,5,6,7-tetrahydroisoindole group, an indole group, a pyridyl group, and further specific examples thereof include a phenoxyfuryl group, a benzylfuryl group, a propargylfuryl group, a methylisoxazolyl group, a trifluoromethylthiazolyl group, a trifluoromethoxythiazolyl group, a propynylpyrrolyl group, a propynyldioxoimidazolidinyl group, a dioxotetrahydroisoindolyl group, an oxothiazolyl group, a halopyridyl group and the like, Examples of the aryl group which may be substituted, represented by $R^6$, include an aryl group, which may be substituted with a phenyl, an alkynyl group, an acyl group, an alkyl group, an alkoxy group, or a halogen atom.

The monohydroxy compound of formula (3) includes, for example, following alkyl alcohol, aralkyl alcohol, aryl alcohol and the like.

Specific examples of the alkyl alcohol include,
methyl alcohol, ethyl alcohol, n-propyl alcohol, isopropyl alcohol, n-butyl alcohol, sec-butyl alcohol, tert-butyl alcohol, n-pentyl alcohol, neopentyl alcohol, n-hexyl alcohol, n-octyl alcohol, n-decyl alcohol, and the like.

Specific examples of the alcohol compound of formula (3) wherein $R^6$ represents the alkyl substituted with a halogen atom include,
fluoroethyl alcohol, difluoroethyl alcohol, trifluoroethyl alcohol, and tetrafluoroethyl alcohol.

Specific examples of the alcohol compound of formula (3), wherein $R^6$ represents a methyl group substituted with a member selected from the alkenyl, haloalkenyl, or alkynyl group include, 4-methylhept-4-en-1-yn-3-ol, 4-fluorohept-4-en-1-yn-3-ol and the like.

Specific examples of the alcohol compound of formula (3), wherein $R^6$ represents a methyl or ethyl group substituted with the heterocyclic group which may be substituted as defined above, include, for example,
2-furylmethyl alcohol, 3-furylmethyl alcohol,
(5-phenoxy-3-furyl)methyl alcohol,
(5-benzyl-3-furyl)methane-1-ol,
{5-(difluoromethyl)-3-furyl}methane-1-ol,
5-propargylfurfuryl alcohol,
(5-methylisoxazole-3-yl)methane-1-ol,
1-{2-(trifluoromethyl)-1,3-thiazole-4-yl}prop-2-yn-1-ol,
1-{2-(trifluoromethoxy)-1,3-thiazole-4-yl}prop-2-yn-1-ol,
1-{1-prop-2-ynyl-5-(trifluoromethyl)pyrrole-3-yl}prop-2-yn-1-ol,
(1-prop-2-ynylpyrrole-3-yl)methane-1-ol,
3-(hydroxymethyl)-1-propynyl-imidazolidine-2,4-dione,
2-(hydroxymethyl)-4,5,6,7-tetrahydroisoindole-1,3-dione,
{1-(2-propynyl)pyrrole-3-yl}methane-1-ol,
5-(hydroxymethyl)-4-methyl-(2-propynyl)-1,3-thiazoline-2-one,
(1-prop-2-ynyl-2-methylindole-3-yl)methane-1-ol,
{1-prop-2-ynyl-2-(trifluoromethyl)indole-3-yl}methane-1-ol,
(2,3,6-trifluoro-4-pyridyl)methane-1-ol, and the like.

Specific examples of the alcohol compound of formula (3), wherein $R^6$ represents a methyl or ethyl group substituted with at least one member selected from the aryl group which may be substituted as defined above, a cyano group; or the alkynyl group, include, for example, aralkyl alcohols such as:
benzyl alcohol, 2-methyl-3-phenylbenzyl alcohol,
2,3,5,6-tetrafluorobenzyl alcohol,
2,3,5,6-tetrafluoro-4-methylbenzyl alcohol,
2,3,5,6-tetrafluoro-4-methoxybenzyl alcohol,
2,3,5,6-tetrafluoro-4-(methoxymethyl)benzyl alcohol,
2,3,5,6-tetrafluoro-4-propargylbenzyl alcohol,
2,3,5,6-tetrafluoro-4-(difluoromethyl)benzyl alcohol,
2,3,5,6-tetrafluoro-4-(difluoromethoxy)benzyl alcohol,
2,3,5,6-tetrafluoro-4-(2,2,2-trifluoroacetyloxy)methylbenzyl alcohol,
4-(trifluoromethyl)benzyl alcohol,
2,3,4,5-tetrafluoro-6-methylbenzyl alcohol,
3-phenylbenzyl alcohol, 2,6-dichlorobenzyl alcohol,
3-phenoxybenzyl alcohol,
2-hydroxy-2-(3-phenoxyphenyl)ethanenitrile,
2-hydroxy-2-{4-(methoxymethyl)phenyl}ethanenitrile,
2-{3-(4-chlorophenoxy)phenyl}-2-hydroxyethanenitrile,
2-(4-amino-2,3,5,6-tetrafluorophenyl)-2-hydroxyethanenitrile,
2-(4-fluoro-3-phenoxyphenyl)-2-hydroxyethanenitrile,
(2-methylphenyl)methyl alcohol,
(3-methylphenyl)methyl alcohol,
(4-methylphenyl)methyl alcohol,
(2,3-dimethylphenyl)methyl alcohol,
(2,4-dimethylphenyl)methyl alcohol,
(2,5-dimethylphenyl)methyl alcohol,
(2,6-dimethylphenyl)methyl alcohol,
(3,4-dimethylphenyl)methyl alcohol,
(2,3,4-trimethylphenyl)methyl alcohol,
(2,3,5-trimethylphenyl)methyl alcohol,
(2,3,6-trimethylphenyl)methyl alcohol,
(3,4,5-trimethylphenyl)methyl alcohol,
(2,4,6-trimethylphenyl)methyl alcohol,
(2,3,4,5-tetramethylphenyl)methyl alcohol,
(2,3,4,6-tetramethylphenyl)methyl alcohol,
(2,3,5,6-tetramethylphenyl)methyl alcohol,
(pentamethylphenyl)methyl alcohol,
(ethylphenyl)methyl alcohol, (n-propylphenyl)methyl alcohol,
(isopropylphenyl)methyl alcohol,
(n-butylphenyl)methyl alcohol,
(sec-butylphenyl)methyl alcohol,
(tert-butylphenyl)methyl alcohol,
(n-pentylphenyl)methyl alcohol,
(neopentylphenyl)methyl alcohol,
(n-hexylphenyl)methyl alcohol,
(n-octylphenyl)ethylalcohol, (n-decylphenyl)methyl alcohol,
(n-dodecylphenyl)methyl alcohol,
(n-tetradecylphenyl)methyl alcohol, naphthylmethyl alcohol,
anthracenylmethyl alcohol, 1-phenylethyl alcohol,
1-(1-naphthyl)ethyl alcohol, 1-(2-naphthyl)ethyl alcohol,
4-prop-2-ynylphenyl)methane-1-ol,
3-prop-2-ynylphenyl)methane-1-ol, and the like.

Examples of the alcohol compound of formula (3), wherein $R^6$ represents 1-, or 2-indanyl group which may be substituted with an alkynyl group or an aryl or heteroaryl group (e.g. thienyl) include, for example,
4-prop-2-enylindan-1-ol, 4-phenylindan-2-ol,
4-(2-thienyl)indan-2-ol, and the like.

Examples of the aryl alcohol includes, phenol, 1-naphthol, 2-naphthol, 4-prop-2-ynylphenol, 3-prop-2-ynylphenol, 4-hydroxyacetophenone, 4-hydroxybenzaldehyde, and the above-described compounds having aromatic rings substituted with an alkyl group, an alkoxy group, a halogen atom, or the like.

Preferred monohydroxy compound (3) are primary alcohols, such as benzyl alcohol, pentafluoroethyl alcohol, 3,3-dibromo-2-propene-1-ol, perfluoropropyl alcohol, hexafluoroisopropyl alcohol, perfluorobutyl alcohol, perfluoropentyl alcohol, perfluorohexyl alcohol, perfluorooctyl alcohol, perfluorodecyl alcohol,
{1-(2-propynyl)-5-(trifluoromethyl)-4-pyrazolyl}methane-1-ol,
1-{(2-propynyl)-5-(trifluoromethyl)pyrrole-3-yl}prop-2-yn-1-ol,
1-{2-(trifluoromethyl)-1,3-thiazole-4-yl}prop-2-yn-1-ol,
1-{2-(trifluoromethoxy)-1,3-thiazole-4-yl}prop-2-yn-1-ol, and 4-fluorohept-4-en-1-yn-3-ol.

Preferred are aralkyl alcohols and hydroxycyclopentenones, and more preferred are:
3-phenoxybenzyl alcohol;
4-hydroxy-3-methyl-2-(2-propenyl)-2-cyclopentene-1-one; and
4-hydroxy-3-methyl-2-(2-propynyl)-2-cyclopentene-1-one, An asymmetric center(s) may be present in the monohydroxy compound (3), and any optical isomer or a mixture thereof may be used in the present process to produce an optically active desired ester(s) (1) with retention of configuration with respect to the asymmetric center(s) in the alcohol moiety.

The monohydroxy compound (3) may be used in excess. Preferably, the monohydroxy compound (3) is used 1 mol or less per mol of the cyclopropanecarboxylic acids (2). After completion of the reaction, unreacted materials may generally be recovered by such operation as distillation, extraction, or the like.

Next, a description will be made to the catalyst compound comprising an element of Group 4 of the Periodic Table of Elements.

Examples of the catalyst compound include a zirconium compound, a titanium compound, a hafnium compound and the like.

Preferred catalyst compounds are zirconium, titanium, and hafnium compounds having Lewis acidity, and can be represented by formula (4):

$$M(O)_m(X)_n(Y)_{4-2m-n} \quad (4)$$

wherein M represents an element of Group 4 of the Periodic Table of Elements; X and Y independently represent a halogen atom, an alkoxy group, an acetylacetonate group, an acyloxy group, an amino group which may be substituted with up to two alkyl groups, or a cyclopentadienyl group; and m is equal to 0 or 1, and n is equal to 0, 1, or 2.

Specific examples of the titanium and hafnium compounds include, for example, titanium halide such as titanium tetrafluoride, titanium tetrachloride, titanium tetrabromide, titanium tetraiodide; titanium acetate, titanium acetylacetonato, titanium ethoxide, titanium i-propoxide, titanium n-butoxide, titanium t-butoxide; titanium oxychloride; titanium amide such as tetrakis(dimethylamino)titanium, tetrakis(diethylamino)titanium or the like; titanocene dichloride, titanocene dimethoxide, decamethyltitanocene dichloride; hafnium halide such as hafnium tetrafluoride, hafnium tetrachloride, hafnium tetrabromide, hafnium tetraiodide or the like; hafnium acetate, hafnium acetylacetonate, hafnium alkoxide such as hafnium ethoxide, hafnium i-propoxide, hafnium n-butoxide, hafnium t-butoxide or the like; hafnium oxychloride; amide compound of hafnium such as tetrakis(dimethylamino) hafnium, tetrakis(diethylamino)hafnium or the like, hafnocene dichloride, hafnocene dimethoxide, and decamethylhafnocene dichloride.

Among the specific compounds, preferred are titanium tetrachloride, titanium i-propoxide, titanocene dichloride, hafnium tetrachloride, hafnium t-butoxide, and hafnocene dichloride.

Specific examples of the zirconium compound includes, for example, zirconium halide such as zirconium tetrafluoride, zirconium tetrachloride, zirconium tetrabromide, zirconium tetraiodide or the like; zirconium acetate, zirconium acetylacetonate; zirconium alkoxide such as zirconium ethoxide, zirconium i-propoxide, zirconium n-butoxide, zirconium t-butoxide or the like; zirconium oxychloride; amide compound of zirconium such as tetrakis (dimethylamino)zirconium, tetrakis(diethylamino) zirconium or the like; zirconocene compound such as zirconocene dichloride, zirconocene dimethoxide, and decamethylzirconocene dichloride. Preferably are zirconium tetrachloride, zirconium t-butoxide, and zirconocene dichloride.

The compound comprising an element of Group 4 of the Periodic Table of Elements may be used as commercially available anhydride or hydrate without any processing. A complex comprising a compound comprising an element of Group 4 of the Periodic Table of Elements and a compound having a ligating property such as tetrahydrofuran and tetramethylethylenediamine may also be used.

Although any amount of the compound comprising an element of Group 4 of the Periodic Table of Elements may be used, it is normally catalytic and preferably around 0.001 to 200 mole % per mol of the cyclopropanecarboxylic acid (2), more preferably within the range of around 0.1 to 20 mole %, and still more preferably within the range of around 0.1 to 10 mole %.

The reaction of the cyclopropanecarboxylic acids (2) with the monohydroxy compound (3) in the presence of the catalyst of the present invention is usually conducted in an inert gas atmosphere such as argon and nitrogen. The reaction may be performed under a normal pressure, a pressurized pressure, or a reduced pressure. Preferably, the reaction is performed under a normal pressure or a reduced pressure. In addition, it is preferable to perform reaction while continuously removing water, which is formed as a byproduct of dehydration reaction, from the reaction system by such a method as distillation or the like.

The reaction may be performed in the absence of a solvent or in a solvent. The solvent that may be used includes: halogenated hydrocarbons such as dichloromethane, chloroform, and 1,2-dichloroethane, aliphatic hydrocarbons such as hexane, heptane; octane, nonane or the like; aromatic hydrocarbons such as benzene, toluene, xylene, chlorobenzene or the like; and ether solvents such as diethyl ether, tetrahydrofuran or the like. By-produced water may be removed from the reaction system by using a solvent that forms an azeotrope with the byproduct water.

Although a reaction temperature is not particularly defined, it is preferably within a range of around 20 to around 200° C.

The catalyst may be removed by washing the reaction mixture with water or acidic water makes, and the cyclopropanecarboxylate esters (1) can be isolated by performing normal operation such as distillation, recrystallization, and column chromatography, if necessary, from the reaction mixtures.

EXAMPLES

The present invention will be described in detail with the following examples, but it is not to be construed that the present invention is limited to the examples.

Example 1

In a 10 ml test tube-type reactor, 0.43 g of 2,2-dimethyl-3-(2-methyl-1-propenyl)cyclopropanecarboxylic acid (E/Z=

80/20), 0.50 g of 3-phenoxybenzyl alcohol, 5.8 mg of zirconium tetrachloride, and 5 ml of xylene were charged. The reactor was equipped with a Dean-Stark trap and a condenser, and the reaction mixture was stirred under reflux for 8 hours at 145° C. while water generated as a by-product during reaction was being separated and collected in the trap. A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 98% (E/Z=84/16, selectivity: 99%) based on the material alcohol.

Example 2

The reaction was performed in a similar manner as in Example 1 except that 9.4 mg of a complex of zirconium tetrachloride with 2-tetrahydrofuran was charged instead of 5.8 mg of zirconium tetrachloride in Example 1.

A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 95% (E/Z=85/15, selectivity: 98%) based on the material alcohol.

Example 3

The reaction was performed in a similar manner as in Example 1 except that 7.3 mg of zirconocene dichloride was charged instead of 5.8 mg of zirconium tetrachloride in Example 1.

A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 97% (selectivity: 98%) based on the material alcohol.

Example 4

The reaction was performed in a similar manner as in Example 1 except that 9.6 mg of zirconium t-butoxide was charged instead of 5.8 mg of zirconium tetrachloride in Example 1.

A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 91% (selectivity, 92%) based on the material alcohol.

Example 5

The reaction was performed in a similar manner as in Example 1 except that 6.6 mg of zirconium acetate was charged instead of 5.8 mg of zirconium tetrachloride in Example 1.

A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 95% (selectivity: 96%) based on the material alcohol.

Example 6

The reaction was performed in a similar manner as in Example 1 except that 0.47 g of (5-benzyl-3-furyl)methane-1-ol was charged instead of 0.50 g of 3-phenoxybenzyl alcohol in Example 1.

A reaction mixture thereof was analyzed with gas chromatography to find that (5-benzyl-3-furyl)methyl 2,2-dimethyl-3-(2-methyl-1-propenyl)cyclopropanecarboxylate was obtained in a yield of 92% (selectivity: 99%) based on the material alcohol.

Comparative Example 1

The reaction was performed in a similar manner as in Example 1 except that 12.5 mg of concentrated sulfuric acid was charged instead of 5.8 mg of zirconium tetrachloride in Example 1.

A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 81% (selectivity: 87%) based on the material alcohol.

Comparative Example 2

The reaction was performed in a similar manner as in Example 1 except that 23.7 mg of p-toluenesulfonic acid was charged instead of 5.8 mg of zirconium tetrachloride in Example 1.

A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 61% (selectivity: 93%) based on the material alcohol.

Example 7

In a 10 ml test tube-type reactor, 0.43 g of 2,2-dimethyl-3-(2-methyl-1-propenyl)cyclopropanecarboxylic acid, 0.38 g of 4-hydroxy-3-methyl-2-(2-propenyl)-2-cyclopentene-1-on, 48.0 mg of zirconium t-butoxide, and 5 ml of xylene were charged. The reactor was equipped with a Dean-Stark trap and a condenser, and the reaction mixture was stirred under reflux for 8 hours at 145° C. while water generated as a by-product during reaction was being separated and collected in the trap. A reaction mixture thereof was analyzed with gas chromatography to find that 3-(2-propenyl)-2-methyl-4-oxo-2-cyclopentenyl 2,2-dimethyl-3-(2-methyl-1-propenyl)cyclopropanecarboxylate was obtained in a yield of 62% (selectivity: 97%) based on the material alcohol.

Example 8

In a 10 ml test tube-type reactor, 0.85 g of 2,2-dimethyl-3-(2-methyl-1-propenyl)cyclopropanecarboxylic acid, 0.75 g of 4-hydroxy-3-methyl-2-(2-propenyl)-2-cyclopentene-1-on, 58 mg of zirconium tetrachloride, and 5 ml of xylene were charged. The reactor was equipped with a Dean-Stark trap and a condenser, and the reaction mixture was stirred under reflux for 16 hours at 145° C. while water generated as a by-product during reaction was being separated and collected in the trap. A reaction mixture thereof was analyzed with gas chromatography to find that 3-(2-propenyl)-2-methyl-4-oxo-2-cyclopentenyl 2,2-dimethyl-3-(2-methyl-1-propenyl)cyclopropanecarboxylate was obtained in a yield of 85% (selectivity; 90%) based on the material alcohol.

Examples 9 to 11

Experiments were conducted in a similar manner as in Example 8 except that the following alcohol compounds and the zirconium compounds were used in place of the alcohol and zirconium compounds used in Example 8.

| Ex. | Alcohol compound | Zirconium compound | Yield (%) of ester | Selectivity (%) |
|---|---|---|---|---|
| 9 | A | Zr[OCH(CH$_3$)$_2$]$_4$ 82 mg | 94 | 94 |
| 10 | B 0.75 g | ZrCl$_4$ | 87 | 87 |
| 11 | B 0.75 g | Zr[OCH(CH$_3$)$_2$]$_4$ 82 mg | 93 | 97 |

A: 4-hydroxy-3-methyl-2-(2-propenyl)-2-cyclopentene-1-on
B: 4-hydroxy-3-methyl-2-(2-propynyl)-2-cyclopentene-1-on A: 4-hydroxy-3-methyl-2-(2-propenyl)-2-cyclopentene-1-on
B: 4-hydroxy-3-methyl-2-(2-propenyl)-2-cyclopentene-1-on

Example 12

In a 10 ml test tube-type reactor, 0.16 g of 2,2-dimethyl-3-(1-propenyl)cyclopropanecarboxylic acid, 0.22 g of 2,3,5,6-tetrafluoro-4-(methoxymethyl)benzyl alcohol, 3.3 mg of zirconium tetraisopropoxide, and 5 ml of xylene were charged. The reactor was equipped with a Dean-Stark trap and a condenser, and the reaction mixture was stirred under reflux for 8 hours at 145° C. while water generated as a by-product during reaction was being separated and collected in the trap. A reaction mixture thereof was analyzed with gas chromatography to find that 2,3,5,6-tetrafluoro-4-(methoxymethyl)benzyl 2,2-dimethyl-3-(1-propenyl)cyclopropanecarboxylate was obtained in a yield of 83% (selectivity: 98%) based on the material alcohol.

Example 13

In a 10 ml test tube-type reactor, 0.34 g of 2,2-dimethyl-3-(2-methyl-1-propenyl)cyclopropanecarboxylic acid, 0.45 g of 2,3,5,6-tetrafluoro-4-(methoxymethyl)benzyl alcohol, 4.7 mg of zirconium tetrachloride, and 5 ml of xylene were charged. The reactor was equipped with a Dean-Stark trap and a condenser, and the reaction mixture was stirred under reflux for 8 hours at 145° C. while water generated as a by-product during reaction was being separated and collected in the trap. A reaction mixture thereof was analyzed with gas chromatography to find that 2,3,5,6-tetrafluoro-4-(methoxymethyl)benzyl 2,2-dimethyl-3-(2-methyl-1-propenyl)cyclopropanecarboxylate was obtained in a yield of 68% (selectivity: 98%) based on the material alcohol.

Examples 14 to 18

Experiments were conducted in a similar manner as in Example 13 except that following zirconium compounds and amounts.

| Ex. | Zirconium compound | Yield of ester (%) | Selectivity (%) |
|---|---|---|---|
| 14 | (ZrCl$_4$) 9.3 mg | 92 | 98 |
| 15 | ZrBr$_4$ 8.2 mg | 62 | 96 |
| 16 | ZrCl$_4$THF complex 7.5 mg | 78 | 99 |
| 17 | Zr[OCH(CH$_3$)$_2$]$_4$ 6.5 mg | 74 | 97 |
| 18 | Zirconocene dichloride, 8.8 mg | 63 | 99 |

Example 19

In a 10 ml test tube-type reactor, 0.43 g of 2,2-dimethyl-3-(2-methyl-1-propenyl)cyclopropanecarboxylic acid, 0.50 g of 3-phenoxybenzyl alcohol, 8.0 mg of hafnium tetrachloride, and 5 ml of xylene were charged. The reactor was equipped with a Dean-Stark trap and a condenser, and the reaction mixture was stirred under reflux for 8 hours at 145° C. while water generated as a by-product during reaction was being separated and collected in the trap. A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 86% (selectivity: 94%) based on the material alcohol.

Example 20

The reaction was performed in a similar manner as in Example 19 except that 11.6 mg of a hafnium tetrachloride•2 tetrahydrofuran complex was charged instead of 8.0 mg of hafnium tetrachloride in Example 19.

A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 97% (selectivity: 98%) based on the material alcohol.

Example 21

The reaction was performed in a similar manner as in Example 19 except that 12.0 mg of a hafnium tetrachloride•2pyridine complex was charged instead of 8.0 mg of hafnium tetrachloride in Example 19.

A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 96% (selectivity: 98%) based on the material alcohol.

Example 22

The reaction was performed in a similar manner as in Example 19 except that 12.5 mg of a hafnium tetrabromide was charged instead of 8.0 mg of hafnium tetrachloride in Example 19. A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 87% (selectivity: 93%) based on the material alcohol.

Example 23

The reaction was performed in a similar manner as in Example 19 except that 10.5 mg of pentamethylcyclopentadienylhafnium trichloride was charged instead of 8.0 mg of hafnium tetrachloride in Example 19.

A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 90% (selectivity, 94%) based on the material alcohol.

Example 24

The reaction was performed in a similar manner as in Example 19 except that 8.9 mg of tetrakis (diethylamino) hafnium was charged instead of 8.0 mg of hafnium tetrachloride in Example 19. A reaction mixture thereof was analyzed with gas chromatography, and the result indicated that (3-phenoxyphenyl)methyl 2,2-dimethyl-3-(2-methyl-1-propenyl)cyclopropanecarboxylate was obtained in a yield of 93% (selectivity: 99%) based on the material alcohol.

Comparative Example 3

The reaction was performed in a similar manner as in Example 19 except that 12.5 mg of concentrated sulfuric acid was prepared instead of 8.0 mg of hafnium tetrachloride in Example 19. A reaction mixture thereof was analyzed with gas chromatography to find that (3-phenoxyphenyl) methyl 2,2-dimethyl-3-(2-methyl-1-propenyl) cyclopropanecarboxylate was obtained in a yield of 81% (selectivity: 87%) based on the material alcohol.

Comparative Example 4

The reaction was performed in a similar manner as in Example 19 except that 23.7 mg of p-toluenesulfonic acid was charged instead of 8.0 mg of hafnium tetrachloride in Example 19. A reaction mixture thereof was analyzed with gas chromatography to find that (3-phenoxyphenyl)methyl 2,2-dimethyl-3-(2-methyl-1-propenyl)cyclopropanecarboxylate was obtained in a yield of 61% (selectivity 93%) based on the material alcohol.

Example 25

In a 10 ml test tube-type reactor were charged 0.43 g of 2,2-dimethyl-3-(2-methyl-1-propenyl)-cyclopropanecarboxylic acid, 0.38 g of 4-hydroxy-3-methyl-2-(2-propenyl)-2-cyclopentene-1-one, 58.1 mg of a hafnium tetrachloride•2tetrahydrofuran complex, and 5 ml of xylene. The reactor was equipped with a Dean-Stark trap and a condenser, and the reaction mixture was stirred under reflux for 8 hours at 145° C. while water generated as a by-product during reaction was being separated and collected in the trap. The resulting reaction mixture was analyzed with gas chromatography to find that 3-(2-propenyl)-2-methyl-4-oxo-2-cyclopentenyl 2,2-dimethyl-3-(2-methyl-1-propenyl) cyclopropanecarboxylate was obtained in a yield of 65% (selectivity: 84%) based on the material alcohol Example 26

The reaction was performed in a similar manner as in Example 25 except that 62.1 mg of a hafnium tetrachloride•2dioxane complex was charged instead of 58.1 mg of a hafnium tetrachloride•2 tetrahydrofuran in Example 25. A reaction mixture thereof was analyzed with gas chromatography to find that 3-(2-propenyl)-2-methyl-4-oxo-2-cyclopentenyl 2,2-dimethyl-3-(2-methyl-1-propenyl) cyclopropanecarboxylate was obtained in a yield of 59% (selectivity: 80%) based on the material alcohol.

Comparative Example 5

The reaction was performed in a similar manner as in Example 25 except that 12.5 mg of concentrated sulfuric acid was charged instead of 58.1 mg of a hafnium tetrachloride•2tetrahydrofuran complex in Example 25. A reaction mixture thereof was analyzed with gas chromatography to find that 3-(2-propenyl)-2-methyl-4-oxo-2-cyclopentenyl 2,2-dimethyl-3-(2-methyl-1-propenyl) cyclopropanecarboxylate was obtained in a yield of 30% (selectivity: 31%) based on the material alcohol.

Comparative Example 6

Reaction was performed in a similar manner as in Example 25 except that 23.7 mg of p-toluenesulfonic acid was charged instead of 58.1 mg of a hafnium tetrachloride•2 tetrahydrofuran complex in Example 25. A reaction mixture thereof was analyzed with gas chromatography to find that 3-(2-propenyl)-2-methyl-4-oxo-2-cyclopentenyl 2,2-dimethyl-3-(2-methyl-1-propenyl)cyclopropanecarboxylate was obtained in a yield of 6.4% (selectivity, 8%) based on the material alcohol.

Example 27

In a 10 ml test tube-type reactor, there were prepared 0.43 g of 2,2-dimethyl-3-(2-methyl-1-propenyl) cyclopropanecarboxylic acid, 0.38 g of 4-hydroxy-3-methyl-2-(2-propynyl)-2-cyclopentene-1-one, 58.1 mg of a complex made of hafnium tetrachloride and 2•tetrahydrofuran, and 5 ml of xylene were charged. The reactor was equipped with a Dean-Stark trap and a condenser, and the reaction mixture was stirred under reflux for 8 hours at 145° C. while water generated as a by-product during reaction was being separated and collected in the trap. A reaction mixture thereof was analyzed with gas chromatography to find that 3-(2-propynyl)-2-methyl-4-oxo-2-cyclopentenyl 2,2-dimethyl-3-(2-methyl-1-propenyl)cyclopropanecarboxylate was obtained in a yield of 61% (selectivity: 79%) based on the material alcohol.

Example 28

The reaction was performed in a similar manner as in Example 27 except that 62.1 mg of a hafnium tetrachloride•2dioxane complex was charged instead of 58.1 mg of a hafnium tetrachloride•2tetrahydrofuran complex in Example 27.

A reaction mixture thereof was analyzed with gas chromatography to find that 3-(2propynyl) -2-methyl-4-oxo-2-cyclopentenyl 2,2-dimethyl-3-(2-methyl-1-propenyl) cyclopropanecarboxylate was obtained in a yield of 58% (selectivity: 79%) based on the material alcohol.

Comparative Example 7

The reaction was performed in a similar manner as in Example 27 except that 12.5 mg of concentrated sulfuric acid was charged instead of 58.1 mg of a hafnium tetrachloride•2tetrahydrofuran complex in Example 27.

A reaction mixture thereof was analyzed with gas chromatography to find that 3-(2-propynyl)-2-methyl-4-oxo-2-cyclopentenyl 2,2-dimethyl-3-(2-methyl-1-propenyl) cyclopropanecarboxylate was obtained in a yield of 9.3% (selectivity: 12%) based on the material alcohol.

Comparative Example 8

The reaction was performed in a similar manner as in Example 27 except that 23.7 mg of p-toluenesulfonic acid was charged instead of 58.1 mg of a hafnium tetrachloride•2tetrahydrofuran complex in Example 27.

A reaction mixture thereof was analyzed with gas chromatography to find that 3-(2-propynyl)-2-methyl-4-oxo-2-cyclopentenyl 2,2-dimethyl-3-(2-methyl-1-propenyl) cyclopropanecarboxylate was obtained in a yield of 0.8% (selectivity: 4.4%) based on the material alcohol.

Example 29

In a 10 ml test tube-type reactor, 0.16 g of 2,2-dimethyl-3-(1-propenyl)cyclopropanecarboxylic acid, 0.22 g of 2,3,5,6-tetrafluoro-4-((methoxymethyl)benzyl alcohol, 4.6 mg of a hafnium tetrachloride•2tetrahydrofuran complex, and 5 ml of xylene were charged. The reactor was equipped with a Dean-Stark trap and a condenser, and the reaction mixture was stirred under reflux for 8 hours at 145° C. while water generated as a by-product during reaction was being separated and collected in the trap. A reaction mixture thereof was analyzed with gas chromatography to find that 2,3,5,6-tetrafluoro-4-(methoxymethyl)benzyl 2,2-dimethyl-3-(1-propenyl)cyclopropanecarboxylate was obtained in a yield of 80% (selectivity: 99%) based on the material alcohol.

Example 30

The reaction was conducted in a similar manner as in Example 29 except that 5.0 mg of hafnium tetrabromide was used in place of 4.6 mg of a hafnium tetrachloride•2tetrahydrofuran complex. Analysis of the reaction mixture showed that the yield of 2,3,5,6-tetrafluoro-4-(methoxymethyl)benzyl 2,2-dimethyl-3-(1-propenyl)cyclopropanecarboxylate was 95% selectivity: 97%) based on the alcohol.

Example 31

In a 10 ml test tube-type reactor, 0.34 g of 2,2-dimethyl-3-(2-methyl-1-propenyl)cyclopropanecarboxylic acid, 0.45 g of 2,3,5,6-tetrafluoro-4-(methoxymethyl)benzyl alcohol, 13.6 mg of a hafnium tetrachloride•2tetrahydrofuran complex, and 5 ml of xylene were charged. The reactor was equipped with a Dean-Stark trap and a condenser, and the reaction mixture was stirred under reflux for 8 hours at 145° C. while water generated as a by-product during reaction was being separated and collected in the trap. A reaction mixture thereof was analyzed with gas chromatography to find that 2,3,5,6-tetrafluoro-4-(methoxymethyl)benzyl 2,2-dimethyl-3-(2-methyl-1-propenyl)cyclopropanecarboxylate was obtained in a yield of 70% (selectivity: 99%) based on the material alcohol.

Example 32

The reaction was conducted in a similar manner as in Example 31 except that 19.9 mg of hafnium tetrabromide was used in place of 18.6 mg of a hafnium tetrachloride•2tetrahydrofuran complex. Analysis of the reaction mixture showed that the yield of 2,3,5,6-tetrafluoro-4-(methoxymethyl)benzyl 2,2-dimethyl-3-(1-propenyl)cyclopropanecarboxylate was 81% (selectivity: 87%) based on the alcohol.

What is claimed is:

1. A process for producing a cyclopropanecarboxylate of formula (1):

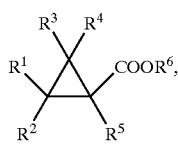
(1)

which process comprises reacting cyclopropanecarboxylic acid of formula (2):

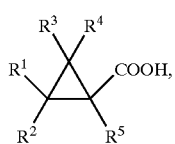
(2)

with a monohydroxy compound of formula (3):

OH (3), in the presence of
a zirconium compound,
wherein $R^1$, $R^2$, $R^3$, $R^4$, and $R^5$ independently represent
a hydrogen atom,
an alkyl group which may be substituted,
an alkenyl group which may be substituted,
an alkynyl group which may be substituted, or
an aryl group which may be substituted; and
$R^6$ represents
an alkyl group which may be substituted, or
an aryl group which may be substituted.

2. A process according to claim 1, wherein
$R^1$, $R^2$, $R^3$, $R^4$, and $R^5$ independently represent
a hydrogen atom,
an alkyl group,
an alkenyl group,
an alkynyl group, or
an aryl group, and
wherein the alkyl, alkenyl, and alkynyl groups may be independently substituted with at least one member selected from
a halogen atom, an alkoxy group,
an alkoxy-carbonyl group,
a haloalkoxy-carbonyl group,
an aryl group,
a halocycloalkylidene group,
an alkoxyimino group,
an alkylsulfonyl group,
an alkylsulfonyloxy group, and
a hydroxysulfinyl group; and
$R^6$ represents
an alkyl group, which may be substituted with a member selected from
a halogen atom, a cyano group, a nitro group,
an alkenyl group, a haloalkenyl group,
an alkynyl group,
an aryl or heterocyclic group which may be substituted with at lest one member selected from:
an alkyl group, a haloalkyl group,
an alkoxy group, a haloalkoxy group,
an alkoxyalkyl group,
an alkenyl group, an alkynyl group,
an aryl group, an aryoxy group,
a haloaryloxy group,
an aralkyl group,
an acyl group,
a haloacyloxyalkyl group,
an amino group, and a halogen atom; or
$R^6$ represents:
a 1-, or 2-indanyl group which may be substituted with an alkynyl group or an aryl or heteraryl group;
a cycloalkenyl group substituted with at least one member selected from an oxo group, an alkyl group, an alkenyl and an alkynyl group; or
an aryl group which may be substituted with a phenyl, an alkynyl group, an acyl group, halogen atom, an alkoxy group, or an alkyl group.

3. A process according to claim 2, wherein
$R^1$, $R^2$, $R^3$, $R^4$, and $R^5$ independently represent
a hydrogen atom,
an (C1–C10) alkyl group,
an (C2–C5) alkenyl group,
an (C2–C5) alkynyl group, or
an (C6–C14) aryl group, and
wherein the alkyl, alkenyl, and alkynyl groups may be independently substituted with at least one member selected from a halogen atom, an (C1–C4) alkoxy group,
an (C1–C4) alkoxy-carbonyl group,
a halo (C1–C4) alkoxy-carbonyl group,
an (C6–C14) aryl group,
a halo (C3–C5) cycloalkylidene group,
an (C1–C3) alkoxyimino group,
an (C1–C4) alkylsulfonyl group,
an (C1–C4) alkylsulfonyloxy group, and
a hydroxysulfinyl group; and $R^6$ represents an (C1–C10) alkyl group, which may be substituted with a member selected from a halogen atom, a cyano group, a nitro group,
an (C2–C5) alkynyl group, a halo (C2–C5) alkenyl group,
an (C2–C5) alkynyl group,
an (C6–C14) aryl or heterocyclic group which may be substituted with at lest one member selected from:
an (C1–C14) alkyl group, a halo (C1–C14) alkyl group,
an (C1–C4) alkoxy group, a halo (C1–C4) alkoxy group,
an (C1–C4) alkoxy (C1–C14) alkyl group,
an (C2–C5) alkenyl group, an (C2–C5) alkynyl group,
an (C6–C14) aryl group, an (C6–C14) aryoxy group,
a halo (C6–C14) aryloxy group,
an (C7–C8) aralkyl group,
an (C1–C2) acyl group,
a haloacyloxy (C1–C14) alkyl group,
an amino group, and a halogen atom; or $R^6$ represents:

a 1-, or 2-indanyl group which may be substituted with an (C2–C5) alkynyl group or an (C6–C14) aryl or 5-membered heteroaryl group;
a cycloalkenyl group substituted with at least one member selected from an oxo group, an (C1–C14) alkyl group, an (C2–C5) alkenyl and an (C2–C5) alkynyl group; or
an (C6–C14) aryl group which may be substituted with a phenyl, an (C2–C5) alkynyl group, a (C1–C2) acyl group, a halogen atom, a (C1–C4) alkoxy group, or a (C1–C14) alkyl group.

4. A process according to claim 1, 2 or 3, wherein the zirconium compound is a compound represented by formula (4):

wherein M represents zirconium; X and Y independently represent a halogen atom, an alkoxy group, an acetylacetonate group, an acyloxy group, an amino group which may be substituted with up to two alkyl groups, or a cyclopentadienyl group; and m is equal to 0 or 1, and n is equal to 0, 1, or 2.

5. A process according to claim 4, wherein the zirconium compound is zirconium tetrachloride, a zirconocene compound, or zirconium alkoxide.

6. A process for producing a cyclopropanecarboxylate of formula (1):

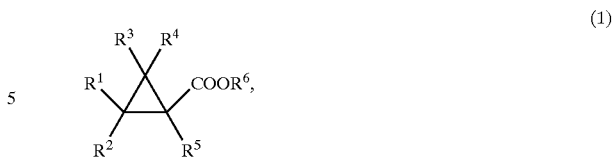

which process comprises reacting cyclopropanecarboxylic acid of formula (2):

with a monohydroxy compound of formula (3):

in the presence of a catalyst compound comprising an element of Group 4 of the Periodic Table of Elements, wherein either $R^1$ or $R^2$ represents 2,2-dichlorovinyl or 2-methyl-1-propenyl group, and the other group represents a hydrogen atom, $R^3$ and $R^4$ represent a methyl group, $R^5$ represents a hydrogen atom, and $R^6$ represents an alkyl group which may be substituted, or an aryl group which may be substituted.

7. A process according to claim 6, wherein $R^6$ represents an alkyl group, which may be substituted with a member selected from a halogen atom, a cyano group, a nitro group,
an alkenyl group, a haloalkenyl group,
an alkynyl group,
an aryl or heterocyclic group which may be substituted with at least one member selected from:
an alkyl group, a haloalkyl group,
an alkoxy group, a haloalkoxy group,
an alkoxyalkyl group,
an alkenyl group, an alkynyl group,
an aryl group, an aryoxy group,
a haloaryloxy group,
an aralkyl group,
an acyl group,
a haloacyloxyalkyl group,
an amino group, and a halogen atom; or $R^6$ represents:

a 1-, or 2-indanyl group which may be substituted with an alkynyl group or an aryl or heteraryl group;
a cycloalkenyl group substituted with at least one member selected from an oxo group, an alkyl group, an alkenyl and an alkynyl group; or
an aryl group which may be substituted with a phenyl, an alkynyl group, an acyl group, halogen atom, an alkoxy group, or an alkyl group.

8. A process according to claim 7, wherein
R⁶ represents
an (C1–C10)alkyl group, which may be substituted with
   a member selected from
a halogen atom, a cyano group, a nitro group,
an (C2–C5)alkenyl group, a halo(C2–C5)alkenyl group,
an (C2–C5)alkynyl group,
an (C6–C14)aryl or heterocyclic group which may be
   substituted with at least one member selected from:
   an (C1–C14)alkyl group, a halo(C1–C14) alkyl group,
   an (C1–C4)alkoxy group, a halo(C1–C4)alkoxy group,
   an (C1–C4)alkoxy(C1–C14)alkyl group,
   an (C2–C5)alkenyl group, an (C2–C5)alkynyl group,
   an (C6–C14)aryl group, an (C6–C14)aryoxy group,
   a halo(C6–C14)aryloxy group,
   an (C7–C8)aralkyl group,
   an (C1–C2)acyl group,
   a haloacyloxy(C1–C14)alkyl group,
   an amino group, and a halogen atom; or
R⁶ represents:
a 1-, or 2-indanyl group which may be substituted with an
   (C2–C5)alkynyl group or an (C6–C14)aryl or
   5-membered heteroaryl group;
a cycloalkenyl group substituted with at least one member
   selected from an oxo group, an (C1–C14)alkyl group,
   an (C2–C5)alkenyl and an (C2–C5)alkynyl group; or
an (C6–C14)aryl group which may be substituted with a
   phenyl, an (C2–C5)alkynyl group, a (C1–C2)acyl
   group, a halogen atom, a (C1–C4)alkoxy group, or a
   (C1–C14)alkyl group.

9. A process according to claim 6, 7 or 8, wherein the catalyst compound is a zirconium, hafnium or titanium compound.

10. A process according to claim 9, wherein the catalyst compound is a zirconium, hafnium or titanium compound having Lewis acidity.

11. A process according to claim 9, wherein the catalyst compound is a compound represented by formula (4):

$$M(O)_m(X)_n(Y)_{4-2m-n} \quad (4)$$

wherein M represents an element of Group 4 of the Periodic Table of Elements; X and Y independently represent a halogen atom, an alkoxy group, an acetylacetonate group, an acyloxy group, an amino group which may be substituted with up to two alkyl groups, or a cyclopentadienyl group; and m is equal to 0 or 1, and n is equal to 0, 1, or 2.

12. A process according to claim 11, wherein M represents zirconium.

13. A process according to claim 11, wherein M represents hafnium or titanium.

14. A process according to claim 12, wherein the zirconium compound is zirconium tetrachloride, a zirconocene compound, or zirconium alkoxide.

15. A process according to claim 13, wherein the hafnium or titanium compound is hafnium or titanium halide, a hafnium or titanium alkoxide, or an amide compound of hafnium or titanium.

16. A process according to claim 6, wherein the monohydroxy compound of formula (3) is a primary alcohol.

17. A process according to claim 7, wherein the monohydroxy compound is a compound of formula (3), wherein R⁶ represents a methyl or ethyl group substituted with at least one member selected from the aryl group which may be substituted, a cyano group, and the alkynyl group.

18. A process according to claim 7, wherein the monohydroxy compound of formula (3) is 3-phenoxybenzyl alcohol.

19. A process according to claim 8, wherein the monohydroxy compound of formula (3) is 4-hydroxy-3-methyl-2-(2-propenyl)-2-cyclopentene-1-one.

20. A process according to claim 8, wherein the monohydroxy compound of formula (3) is 4-hydroxy-3methyl-2-(2-propynyl)-2-cyclopentene-1-one.

21. A process for producing a cyclopropanecarboxylate of formula (1):

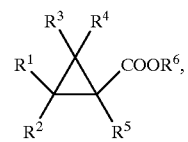

(1)

which process comprises reacting cyclopropanecarboxylic acid of formula (2):

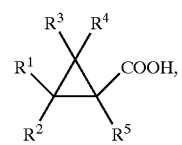

(2)

with a monohydroxy compound of formula (3):

$$R^6OH \quad (3)$$

in the presence of
a catalyst compound comprising an element of Group 4 of
   the Periodic Table of Elements,
wherein R¹, R², R³, R⁴, and R⁵ independently represent
   a hydrogen atom, a halogen atom,
   an alkyl group which may be substituted,
   an alkenyl group which may be substituted,
   an alkynyl group which may be substituted, or
   an aryl group which may be substituted; and
R⁶ represents
   3-methyl-2-(2-propenyl)-2-cyclopentene-1-one-4-yl
      group, or 3-methyl-2-(2-propeynyl)-2-cyclopentene-1-
      one-4-yl group.

22. A process according to claim 21, wherein
R¹, R², R³, R⁴, and R⁵ independently represent
   a hydrogen atom, a halogen atom,
   an alkyl group,
   an alkenyl group,
   an alkynyl group, or
   an aryl group, and
   wherein the alkyl, alkenyl, and alkynyl groups may be
      independently substituted with at least one member
      selected from
   a halogen atom, an alkoxy group,
   an alkoxy-carbonyl group,
   a haloalkoxy-carbonyl group,
   an aryl group,
   a halocycloalkylidene group,
   an alkoxyimino group,
   an alkylsulfonyl group,
   an alkylsulfonyloxy group, and
   a hydroxysulfinyl group.

23. A process according to claim 22, wherein $R^1$, $R^2$, $R^3$, $R^4$, and $R^5$ independently represent a hydrogen atom, a halogen atom, an (C1–C10)alkyl group, an (C2–C5)alkenyl group, an (C2–C5)alkynyl group, or an (C6–C14)aryl group, and wherein the alkyl, alkenyl, and alkynyl groups may be independently substituted with at least one member selected from a halogen atom, an (C1–C4)alkoxy group, an (C1–C4)alkoxy-carbonyl group, a halo (C1–C4)alkoxy-carbonyl group, an (C6–C14)aryl group, a halo(C3–C5)cycloalkylidene group, an (C1–C3)alkoxyimino group, an (C1–C4)alkylsulfonyl group, an (C1–C4)alkylsulfonyloxy group, and a hydroxysulfinyl group.

24. A process according to claim 22, or 23, wherein the catalyst compound is a zirconium, hafnium or titanium compound.

25. A process according to claim 24, wherein the catalyst compound is a zirconium, hafnium or titanium compound having Lewis acidity.

26. A process according to claim 24, wherein the catalyst compound is a compound represented by formula (4):

$$M(O)_m(X)_n(Y)_{4-2m-n} \quad (4)$$

wherein M represents an element of Group 4 of the Periodic Table of Elements; X and Y independently represent a halogen atom, an alkoxy group, an acetylacetonate group, an acyloxy group, an amino group which may be substituted with up to two alkyl groups, or a cyclopentadienyl group; and m is equal to 0 or 1, and n is equal to 0, 1, or 2.

27. A process according to claim 26, wherein M represents zirconium.

28. A process according to claim 26, wherein M represents hafnium or titanium.

29. A process according to claim 27, wherein the zirconium compound is zirconium tetrachloride, a zirconocene compound, or zirconium alkoxide.

30. A process according to claim 28, wherein the hafnium or titanium compound is hafnium or titanium halide, a hafnium or titanium alkoxide, or an amide compound of hafnium or titanium.

31. A process for producing a 2,2-dimethyl-3-(1-propenyl)cyclopropanecarboxylate, which process comprises:

reacting a 2,2-dimethyl-3-(1-propenyl)cyclopropanecarboxylic acid with a monohydroxy compound of formula (3):

$$R^6OH \quad (3),$$

in the presence of a zirconium compound, wherein $R^6$ represents an alkyl group which may be substituted, or an aryl group which may be substituted.

* * * * *